(12) United States Patent
Martino

(10) Patent No.: US 6,637,884 B2
(45) Date of Patent: Oct. 28, 2003

(54) ABERROMETER CALIBRATION

(75) Inventor: Ronald J. Martino, Geneva, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 98 days.

(21) Appl. No.: 10/017,349

(22) Filed: Dec. 14, 2001

(65) Prior Publication Data

US 2003/0112411 A1 Jun. 19, 2003

(51) Int. Cl.[7] ................................. A61B 3/10
(52) U.S. Cl. ...................................... 351/212
(58) Field of Search ............................. 351/205, 206, 351/208, 211, 212, 221, 246

(56) References Cited

U.S. PATENT DOCUMENTS

| | | | |
|---|---|---|---|
| 5,777,719 A | 7/1998 | Williams et al. ............ | 351/212 |
| 6,409,345 B1 * | 6/2002 | Molebny et al. ............ | 351/212 |
| 6,561,648 B2 * | 5/2003 | Thomas ....................... | 351/221 |
| 6,565,209 B2 * | 5/2003 | Campin ....................... | 351/212 |

* cited by examiner

Primary Examiner—George Manuel
(74) Attorney, Agent, or Firm—William Greener

(57) ABSTRACT

A wavefront sensor for measuring ocular aberrations includes a calibration test component and comparative calibration measurement information stored in the device to insure that the device is properly calibrated for reliable aberration measurement. Wavefront calibration, focusing calibration, and retinal illumination level monitoring are contemplated calibration measurements. An optional interlock function prevents diagnostic/therapeutic operation of the aberrometer if it is out of calibration or unsafe for use. A method for calibrating an aberrometer is described.

24 Claims, 7 Drawing Sheets

Interferograms of an Example surface of the form: $\rho^3 \cos 3\theta$

ABERROMETER CALIBRATION

BACKGROUND OF THE INVENTION

1. Field of the Invention

The present invention pertains to the field of ophthalmic wavefront sensing and, particularly, to apparatus and associated methods for aberrometer calibrations.

2. Description of Related Art

A wavefront sensor, often referred to as an aberrometer (which term will be used interchangeably herein), is a device that measures a difference in the optical path of light between a deformed wavefront and an ideal, or reference, wavefront. The measurement, when properly processed, yields values for various aberrations in the optical system that the light propagates through, and which deform the wavefront. Although high-energy lasers and astronomical imaging were primary drivers for wavefront sensor development (where the atmosphere itself was the aberration causing optical system), more recent attention has focused on measuring the aberrations of the eye with the goal of improving visual quality. The interested reader is directed to Geary, J M, Introduction to Wavefront Sensors, SPIE Optical Engineering Press (1995); Williams' U.S. Pat. No. 5,777,719, for more information. These references, to the extent permitted by applicable patent rules and laws, are herein incorporated by reference in their entirety.

The aforementioned Williams' patent describes a Shack-Hartmann type wavefront sensing instrument that can be used to measure, among other parameters, higher-order ocular aberrations. Many commercial aberrometers incorporate a microlens (lenslet) array and operate on the Shack-Hartmann principle. Other types of aberrometers include the spatially resolved refractometer based on the Scheiner optometer, those based on the Tscherning principle, Skiascopic systems, scanning systems of the Tracey technology type, raytracing devices, and others. All of these aberrometer types are well known in the ophthalmic wavefront sensing art so that a detailed description of these devices is not necessary to understand the invention. Descriptions of these devices can be found, for example, in *J Refractive Surg.* 16 (5), September/October 2000.

Ocular wavefront data is increasingly being used to configure ablation algorithms for refractive surgery such as, e.g., PRK, LASIK, and LASEK, and for custom shaping of contact lenses, IOLs, onlays and other vision correcting elements. Successful outcomes to these applications depend upon the validity of the obtained aberration measurement which in turn depends on the correct initial calibration of the aberrometer, and on the correct calibration of the aberrometer when it is used to obtain diagnostic/therapeutic wavefront aberration measurements. Accordingly, the inventor has recognized a need for a method and apparatus that addresses these concerns and others relating to the accuracy and reproducibility of wavefront measurement and aberrometer operation.

SUMMARY OF THE INVENTION

An embodiment of the invention is directed to an improved wavefront sensing device. An aberrometer, regardless of its operating principle, requires an optical head, a data acquisition, storage and processing system for detecting, measuring and displaying wavefront aberration data, and interlinking electronics and software. The improvement according to the invention is characterized generally by an aberrometer calibration component located in an optical path of the wavefront sensor, and an archived calibration measurement of the calibration component that accurately represents a desired measurement parameter of the calibration component. The calibration component preferably comprises a well-characterized test optic or model eye. In a preferred aspect of this embodiment for wavefront measurement calibration, the calibration component is a model eye having a known wavefront aberration, and the desired measurement parameter is a Zernike aberration coefficient for making a wavefront measuring calibration. In another aspect relating to aberrometer refractive focusing calibration, the calibration component is a test optic having a known plus or minus dioptric power, and the desired measurement parameter is a refractive calibration or aberrometer focusing calibration. These calibration components may be used exclusively or in combination. One or more controllable light transmitting elements, e.g., shutters or apertures, are disposed in the optical path to selectively transmit light to and from the calibration components such that calibration and diagnostic/therapeutic measurements can be separately obtained. In addition to the calibration component(s), a light intensity or power meter is disposed between the retinal illumination source of the aberrometer and the patient's eye to provide a safety function against dangerously high (or inadequately low) levels of retinal illumination. Any or all of the aforementioned components can be cooperatively engaged with an interlinking aberrometer processing and control center to prevent diagnostic and/or therapeutic operation of the aberrometer if it is out of calibration or unfit or unsafe for use.

The invention further contemplates associated calibration and monitoring methods of operation.

These and other objects of the present invention will become more readily apparent from the detailed description to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

DETAILED DESCRIPTION OF PREFERRED EMBODIMENTS

Figure 1:
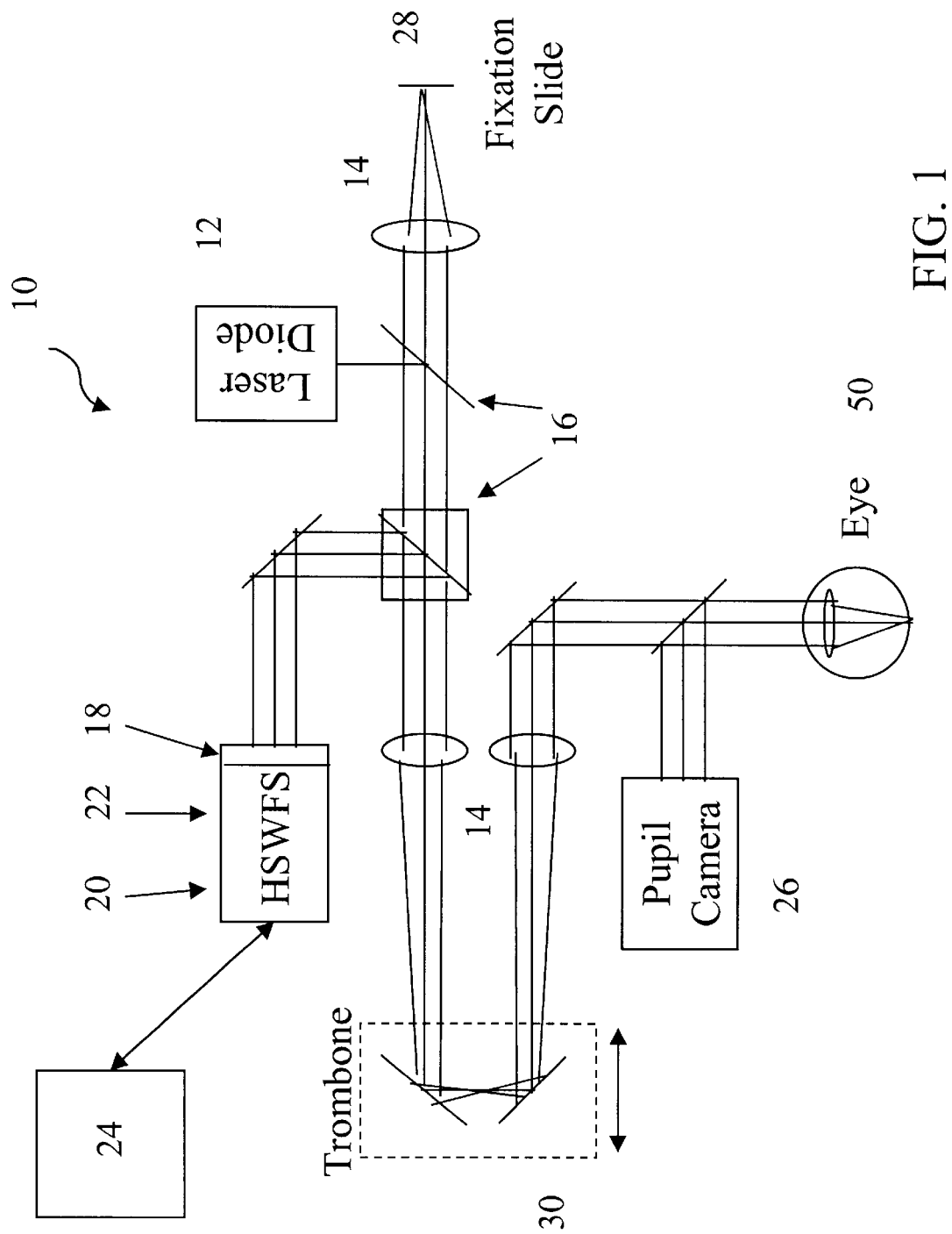
FIG. 1 is an optical schematic diagram of a generic Shack-Hartmann aberrometer.

FIG. 1 shows an optical diagram of a generic Shack-Hartmann aberrometer 10. It will be appreciated that the invention is not limited to a Shack-Hartmann aberrometer, but in fact applies to all aberrometers and wavefront sensing methods that are amenable to a test object in a measurement path of the aberrometer and comparative analysis of a stored, calibrated measurement with a calibration measurement of the test optic. The term "dioptric power" as used herein refers to (±) spherical defocus measured in diopters (D) as is produced by a spherical convex or concave lens, or the eye.

In general terms describing wavefront sensor operation, a patient's eye is properly aligned with the measurement axis of the aberrometer. The retina of the eye is illuminated by a source of light such as a laser diode, for example, or other appropriately coherent or semi-coherent source, and the light is focused on the retina by an optical system in the aberrometer. Reflected light from the retina passes out through the eye's optical system and on to a detector. In the Shack-Hartmann system, which currently is the dominant ophthalmic device methodology for diagnostic wavefront measurement, the reflected light is focused by a lenslet array into aerial images on the detector. Image centroids are calculated and wavefront slope data is obtained from image displacement information. The information is processed and typically fit to Zernike polynomials to output the aberration coefficient measurements. These coefficients can then be used in the design of corrective lenses, ablation algorithms, and in other ophthalmic applications known to those skilled in the art.

Referring to FIG. 1, an aberrometer 10 generically requires an optical head, a data acquisition, storage and processing system for detecting, measuring and displaying wavefront aberration data, and interlinking electronics and software. The optical head preferably encompasses a laser diode illumination source 12 operating at 780 nm (other wavelengths are also suitable as is known in the art); imaging lenses 14 and beam splitters 16 for manipulating transmitted and reflected light from the illumination source 12; a lenslet array 18 for imaging light reflected from the eye's retina on a detector or sensor 20; a wavefront camera 22 incorporated with the sensor, and display monitor (not shown) for viewing the imaged spots; a processing system 24 which includes a P.C. and appropriate software for calculating the aberration data, for command and control of aberrometer components, for data transfer, and for various calculations using the wavefront information; and an alignment camera 26 to aid in eye positioning. A fixation target 28 typically aids in the alignment and measurement of the patient's eye 50. Preferably, the fixation target will be backlighted by a green emitting LED as green provides better accommodation than red light. The wavefront-sensing device 10 includes an optical trombone system 30 to compensate for the dioptric refraction (defocus) introduced by the patient's eye. In other words, the trombone system (or an alternate optical focusing system known in the art) is used to compensate for the simple near- or far-sightedness in the eye and also sharpens the focus of the image spots formed on the detector, resulting in more accurate wavefront measurement. The interested reader is referred to International Publication WO 01/28408 for a detailed description of the optical trombone system. This publication is incorporated herein by reference in its entirety to the extent permitted by applicable patent rules and laws.

Figure 2:
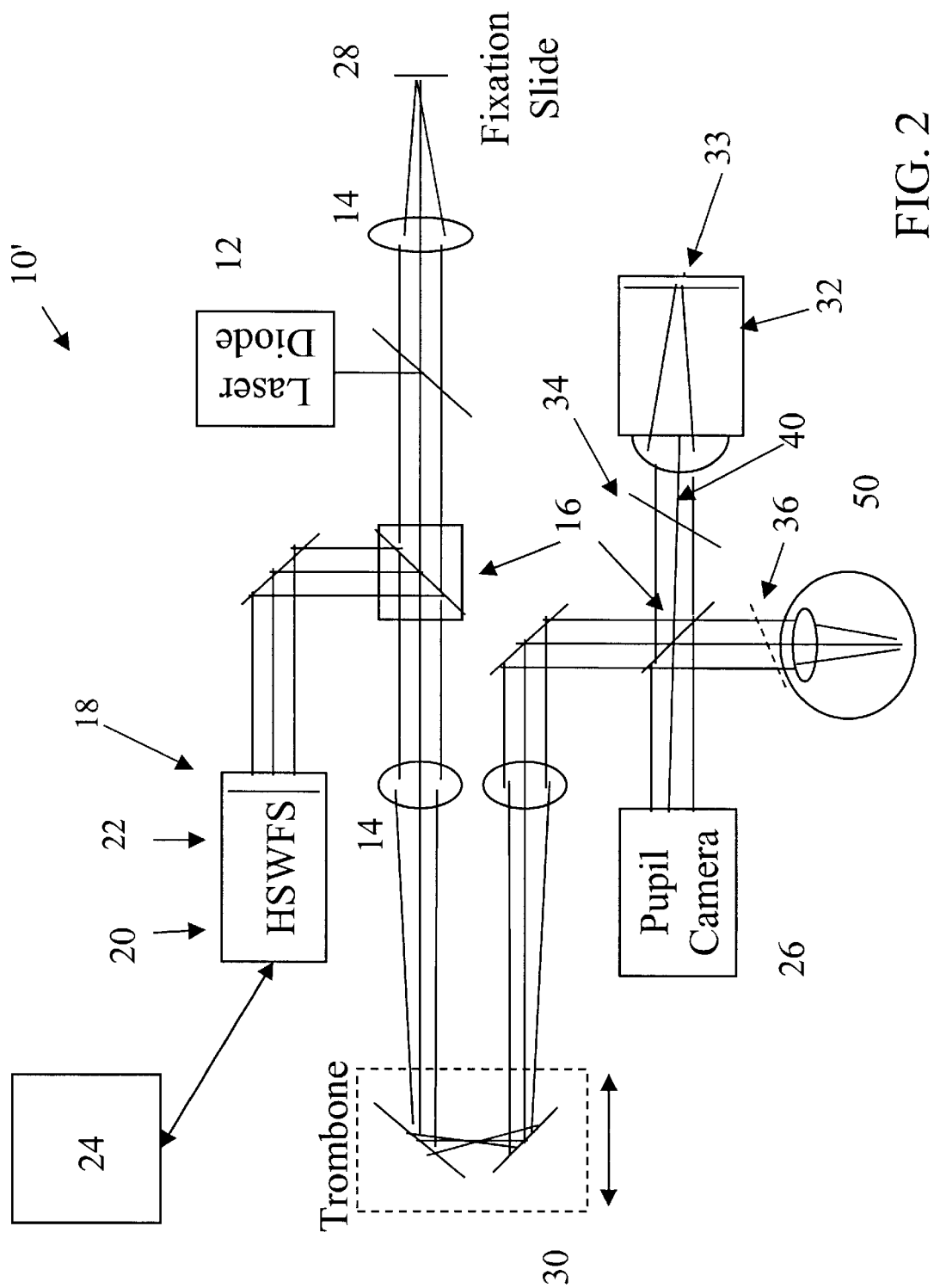
FIG. 2 is an optical schematic diagram of a Shack-Hartmann aberrometer according to an embodiment of the invention.
Figure 7:
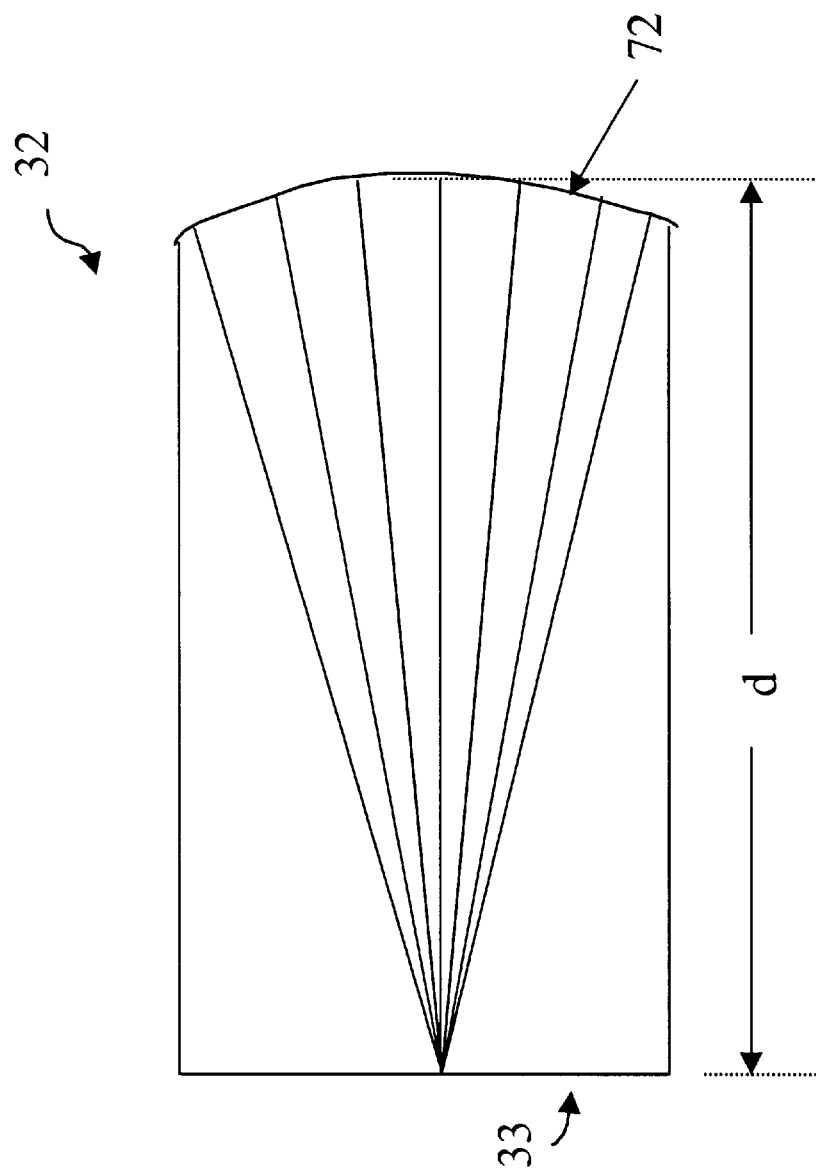
FIG. 7 is a line drawing of an exemplary model eye according to the invention.

According to an embodiment of the invention as shown in FIG. 2, an improved wavefront sensor 10' includes a wavefront calibration test lens 32 (described in more detail below) located in an optical measurement path 40. Preferably, the test lens 32 has been carefully made and accurately characterized to serve as a calibration element. A reflecting surface or medium 33 is provided preferably on the back surface of the test lens 32 to simulate the diffuse scattering by the retina. The location of surface 33 need not be integral with, or immediately adjacent, the test lens surface but can be suitably located as appreciated by one skilled in the art. In an aspect where the test optic is a model eye as illustrated in FIG. 7 and described below, the reflecting surface 33 is located a distance d from the anterior model eye surface 72 to simulate that distance in a human eye. In a preferred aspect, a controllable light transmitting element (LTE) 34 such as, but not limited to, a mechanically, electrically, or optically controlled shutter or aperture 34, is positioned along the optical axis 40 between the illumination source 12 and the test optic 32. The LTE 34 is opened to allow light from source 12 to propagate through the test lens 32 for calibration, and closed otherwise. The LTE is oriented at a slight angle with respect to optical axis 40 such that any light reflected from a surface of the LTE will not travel back to the detector 20 and/or wavefront camera 22. Another, optional LTE 36, similar to LTE 34, is disposed between the source 12 and the eye 50 to allow light propagation to the eye during a diagnostic or therapeutic wavefront measurement and to block light to the eye during the calibration measurement.

Figure 6:
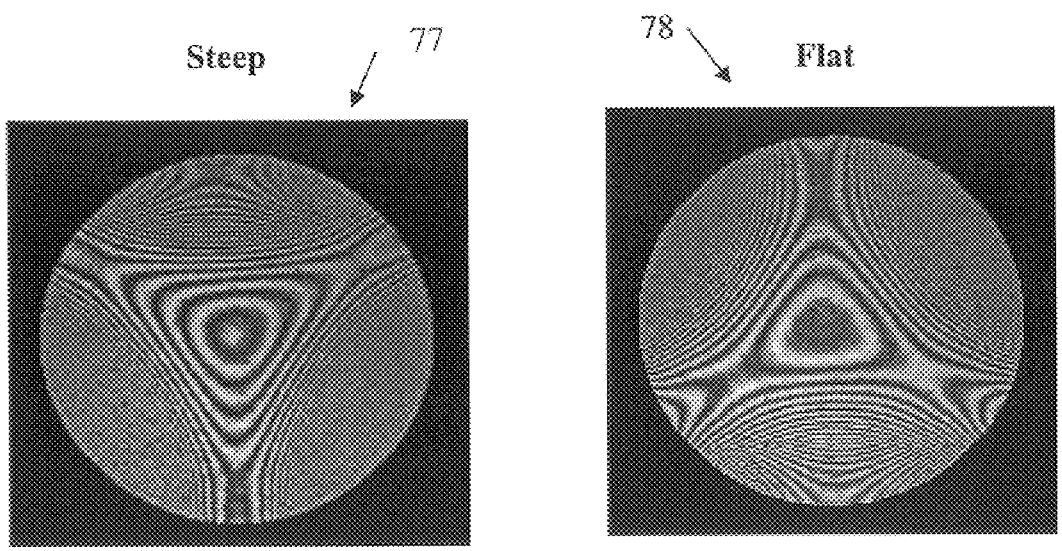
FIG. 6 is a reproduction of an optical interferogram of the anterior surface of an exemplary model eye according to the invention.

In a preferred aspect of this embodiment, the test optic 32 is a model eye as illustrated in FIG. 7. The model eye 32 is a monolithic, plano-convex optic, in which the convex (anterior) surface 72 may be a sphere, an axisymmetric asphere, or a non-axisymmetric asphere, depending upon what aberrations are to be simulated. Both the convex and plano surfaces of model eye 32 can be formed by conventional fabrication techniques including grinding and polishing, diamond turning, laser machining, etching, molding, etc. Material for the model eye can be any optical material that is transparent at the illumination wavelength of interest, including glass (e.g., BK7), plastic (e.g., PMMA), crystal, and poly-crystalline materials (e.g., ZnS). In an exemplary embodiment, the model eye 32 is a diamond-turned plano-convex cylinder of PMMA. The axial length, d, is 23.647 mm with an outer diameter of 12.7 mm. The prescription of the convex surface is as follows:

Vertex Radius, R=7.8 mm;
Conic Constant, k=0;
Coefficient for the 11th Zernike Term, Z330= 0.008652619 mm;
Normalization Radius, NR=4 mm;
Equation for the Sag of the Surface:

$$Z=(x^2/R)/[1+sqrt(1-(1+k)*(x/R)^2]+Z330*(x/NR)^3*cos(3q)$$

where x is the radial coordinate in millimeters and q is the azimuthal coordinate in degrees or radians. The model eye 32 exhibits 1.89 micron of trefoil over an aperture of 5.7 mm at 780 nm. Interferograms 77,78 of the anterior surface of the model eye are shown in FIG. 6.

Figure 3:
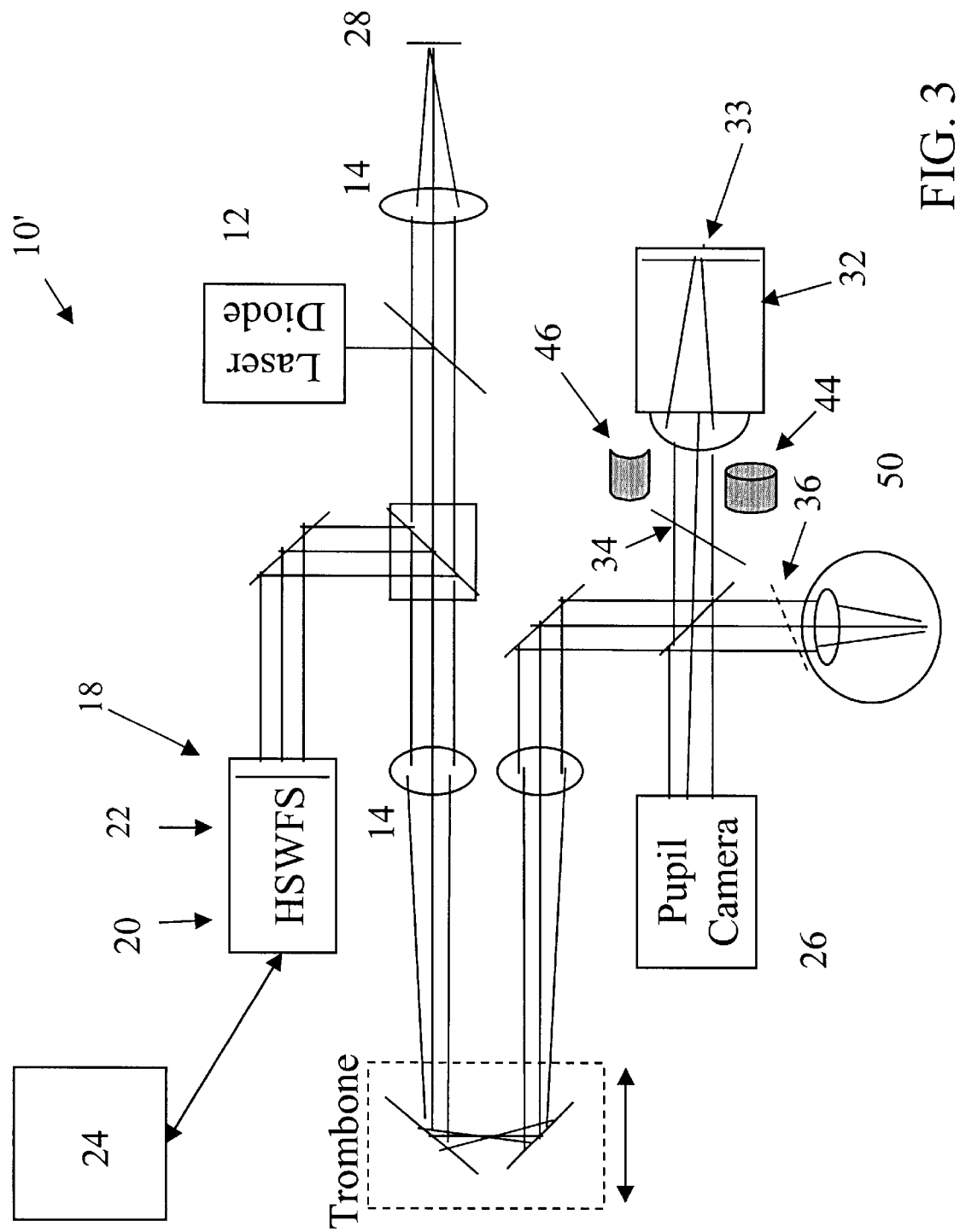
FIG. 3 is an optical schematic diagram of a Shack-Hartmann aberrometer according to another embodiment of the invention.

In another embodiment illustrated schematically in FIG. 3, the calibration component is preferably one of a positive spherical lens 44 or a negative spherical lens 46 disposed along optical axis 40 via a turret assembly, V-groove, or other well known insertion/holding device. The desired calibration parameter is the dioptric focus setting of the trombone system 30. The lens 44 (46) has a known dioptric focusing power preferably in the range of ±10 D. When the lens 44 is positioned in the system as shown, the trombone optical system 30 is adjusted to compensate for the particular dioptric power of the lens. The initial calibration focus setting is stored in a storage medium of the processing center 24 of the aberrometer. At some later time, the test lens 44 (46) can again be accurately positioned in the measurement path of the aberrometer and the focus setting of the trombone system can be compared to the stored measurement data. If the aberrometer is within a suitable focus calibration range, preferably to within about ±0.25 D, then the aberrometer is calibrated for focus power; otherwise, recalibration will be recommended. A safety interlock system can be made available in the aberrometer's control system 24 to prevent diagnostic/therapeutic operation of the aberrometer if it is not in a preset calibration range.

Figure 4B:
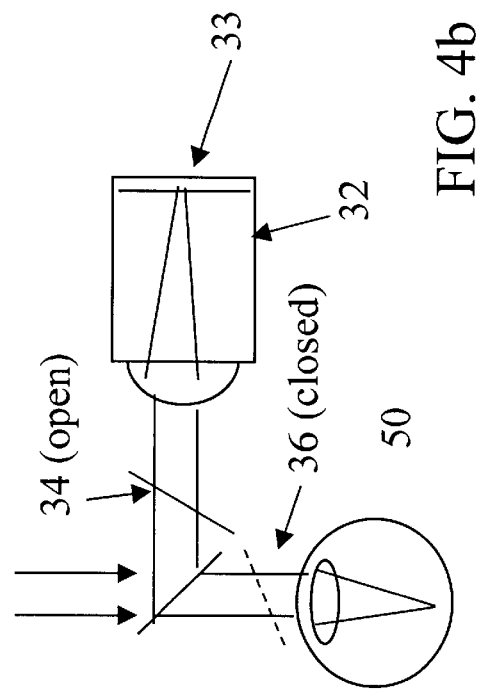
FIGS. 4(a–d) are optical line illustrations of various calibration aspects according to an embodiment of the invention.
Figure 4D:
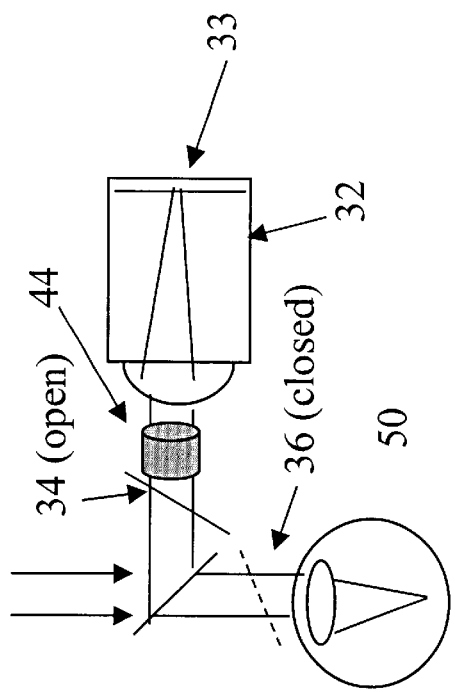
Figure 4A:
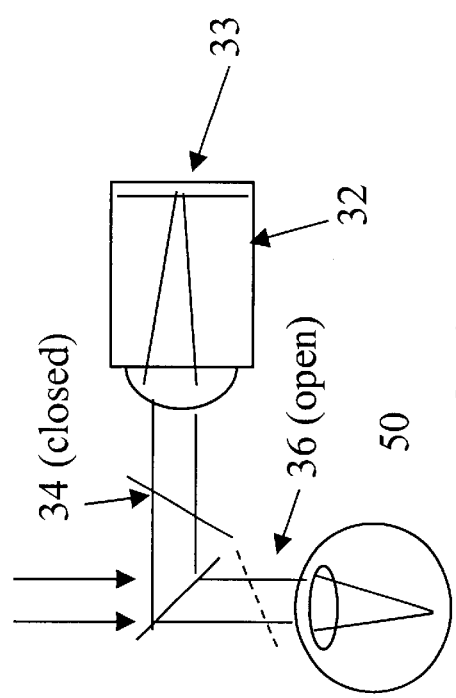
Figure 4C:
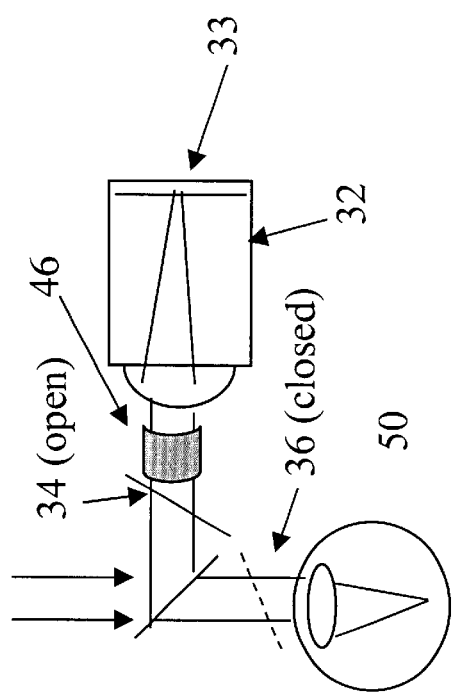

In a preferred aspect, both the wavefront calibration component 32 and the focus calibration component(s) 44 (46) will be available for calibration of the aberrometer. FIGS. 4 (a–d) show four calibration measurement scenarios according to the invention. FIG. 4a illustrates the diagnostic/therapeutic eye measuring mode in which wavefront calibration lens 32 is permanently positioned in optical path 40, however, shutter 34 is closed thus blocking the transmission of light to the test optic. Light from laser 12 is reflected from beamsplitter 16 into eye 50 for wavefront measurement of the eye. In FIG. 4b, shutter 36 is closed to block the transmission of light into the eye while shutter 34 is open to propagate light from source 12 to the wavefront calibration lens 32. The measured aberrations are compared to previously obtained and stored wavefront calibration data and aberrometer calibration is verified. FIG. 4c shows negative dioptric power lens 46 positioned in the optical path 40 along with wavefront calibration lens 32. Similarly, in FIG. 4d, positive lens 44 is in calibration measurement position with shutter 34 open and shutter 36 closed. Comparative measurements between stored trombone position and measurements obtained from system 4c or 4d provide for focusing calibration of the aberrometer.

Figure 5:
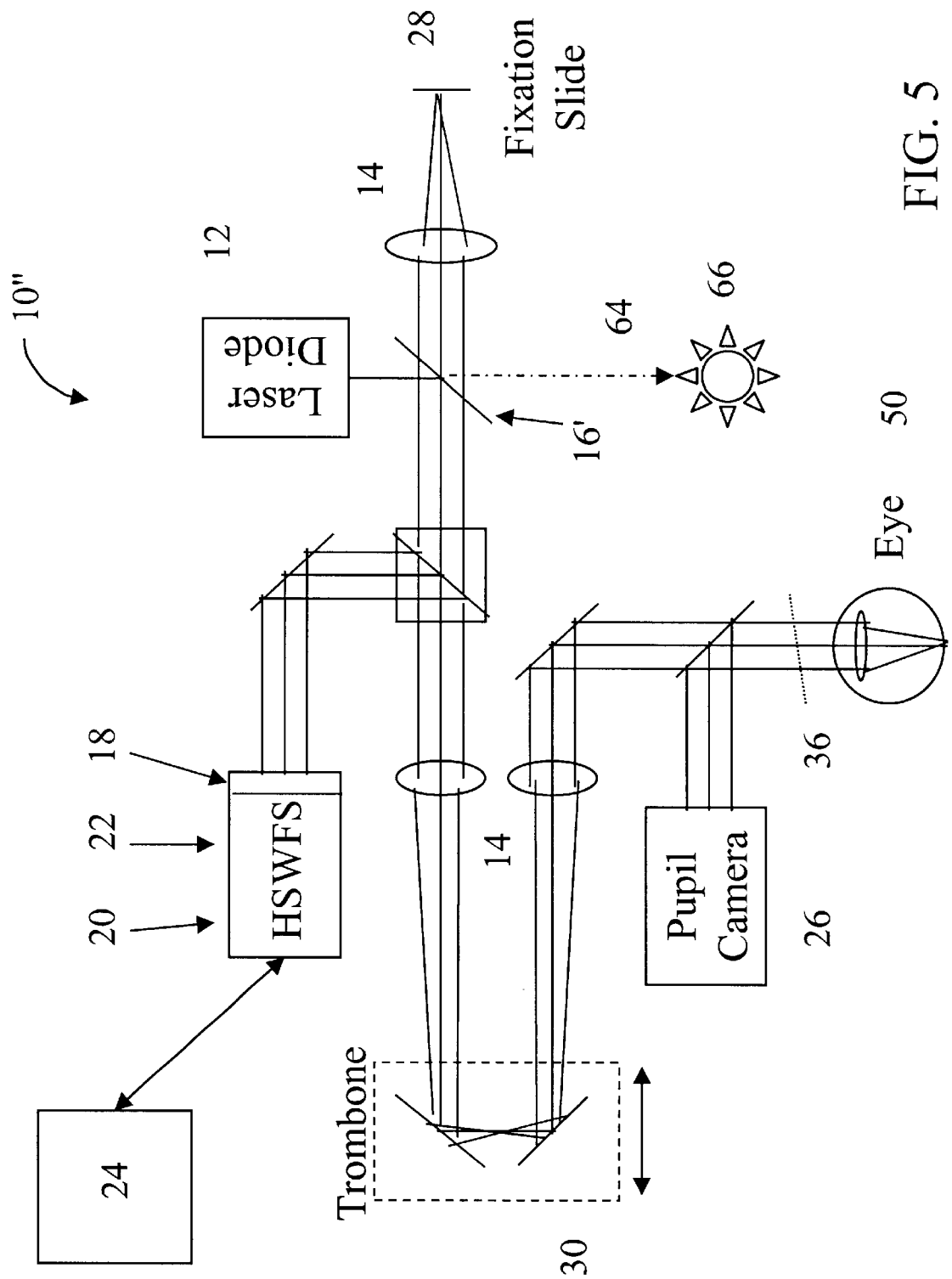
FIG. 5 is an optical schematic diagram of another calibration aspect according to an embodiment of the invention.

In another embodiment in accordance with FIG. 5, a retinal illumination level measuring device 66 is disposed in optical path 64 in line with illumination source 12. Preferably, the illumination source is a laser emitting 780 nm light, and the measuring device 66 is a laser power meter. In order to monitor laser power continuously, the power meter 66 is permanently positioned in beam path 64 provided by beamnsplitter 16'. The appropriate lid transmission/reflection ratio of beamsplitter 16' will be determined by the available laser power. The aberrometer control software in processor 24 can be programmed, for example, to automatically pulse the laser immediately prior to injection into the eye 50 which is protected by controllable shutter 36. If the measured power is too high (or low), the interlock system of the aberrometer can warn the operator or disable the aberrometer operation until any problem is resolved. This aspect of the invention is preferably a complimentary function with the other calibration measurements referred to herein.

According to another embodiment of the invention, a method for calibrating an aberrometer involves the following steps: A test element having a known characterization, such as, but not limited to, a wavefront deformation and/or a dioptric power, is provided in a measurement path of the device. An initial calibration of the aberrometer is made using the test element to provide accurate measurement calibration data of the desired nature. The measurement calibration data is stored in a storage medium, e.g., the P.C., of the device. A test measurement of the test element is then made at a selected time. This could occur prior to every diagnostic wavefront measurement, at preset time intervals, or manually. The test measurement is then compared with the stored calibration measurement data and the calibration of the wavefront sensor is verified when the comparison falls within a predetermined calibration tolerance range. Foe example, if it is desired to measure each Zernike coefficient to within ±0.25 waves, then the calibration tolerance would be set to approximately ±0.1 waves. A focusing tolerance range for the trombone focusing system is preferably about ±0.25 D. If verification does not occur, the wavefront sensor can be recalibrated by the appropriate personnel.

Illustratively, a wavefront calibration measurement will preferably involve the steps of capturing an initial set of wavefront data from the test optic that is known to be accurate, calculating the Zernike coefficients of the measured aberrations and storing the Zernike coefficients in a memory medium/location of the device, obtaining, at some later time, another set of wavefront data from the test optic and again calculating the associated Zernike coefficients, and comparing these two coefficient data sets to verify the aberrometer calibration. Other calibration steps and calibration tolerances can obviously be chosen as desired for a particular application, within the scope of the present invention.

While various advantageous embodiments have been chosen to illustrate the invention, it will be understood by those skilled in the art that changes and modifications can be made therein without departing from the scope of the invention as defined in the appended claims.

I claim:

1. An improved wavefront sensor device for measuring ocular aberrations, said wavefront sensor including an optical head, a data acquisition, storage and processing system, and interlinking electronics integrated to detect, measure and display ocular aberration information from light reflected from a retina of an eye, the improvement characterized by:

a wavefront sensor calibration component cooperatively engaged with the wavefront sensor; and an archived calibration measurement data that accurately represents a desired measurement parameter of the calibration component.

2. The device of claim 1, wherein the calibration component is a test optic having the desired measurement parameter.

3. The device of claim 2, wherein the desired measurement parameter is at least one of a known wavefront deformation and a known optical power.

4. The device of claim 1, wherein the calibration component includes a test optical element having the desired measurement parameter; and further comprising at least one means for controllably transmitting light to the test optic.

5. The device of claim 4, including another means for controlling light transmission to the eye being tested.

6. The device of claim 4, wherein the light transmitting means is oriented in such a manner with respect to an optical axis of the device that light reflected from the light transmitting means does not propagate along the optical axis of the device.

7. The device of claim 4, wherein the at least one light transmitting means is cooperatively engaged with the data acquisition, storage and processing system of the device.

8. The device of claim 1, further comprising an interlock providing element that prevents diagnostic/therapeutic operation of the aberrometer if the device is outside of a predetermined calibration range.

9. The device of claim 1, wherein the wavefront sensor device is a Shack-Hartmann wavefront sensor.

10. The device of claim 1, wherein the wavefront sensor device is a Tscherning aberrometer.

11. The device of claim 1, wherein the wavefront sensor device is a raytracing aberrometer.

12. The device of claim 1, wherein the wavefront sensor device is a skiascopic aberrometer.

13. The device of claim 1, further including a scattering medium associated with the calibration component that simulates light scatter from the retina of the eye.

14. The device of claim 1, wherein the calibration component includes a first component in an optical path of the aberrometer that provides a wavefront calibration measurement, and a second component intermediate the first component and a wavefront sensor element that provides a refractive power calibration measurement.

15. The device of claim 14, wherein the second component includes an optical element having a dioptric power in a range between about ±10 D.

16. The device of claim 14, wherein the second component can be selectively positioned in or out of the optical path.

17. The device of claim 1, further comprising a retinal illumination level measuring device disposed between a retinal illumination source and the eye.

18. The device of claim 17, wherein the retinal illumination source is a least one of a partially coherent and a coherent light emitting source.

19. A method for calibrating an aberrometer, comprising:

locating a test element having a known measurement parameter in an optical path of the aberrometer;

making an initial measurement of the known measurement parameter using the aberrometer to obtain aberrometer calibration data;

storing the calibration data in a storage medium of the aberrometer;

making a test measurement of the test element at a selected time;

comparing the test measurement with the stored calibration data; and verifying the calibration of the aberrometer within a pre-determined calibration range.

20. The method of claim 19, wherein the known measurement parameter is a wavefront deformation.

21. The method of claim 19, wherein the known measurement parameter is a dioptric power.

22. The method of claim 19, wherein locating a test element includes locating a first component in an optical path of the aberrometer that provides a wavefront calibration measurement, and a second component intermediate the first component and a wavefront sensor element that provides a refractive power calibration measurement.

23. The method of claim 19, further comprising recalibrating the aberrometer if it is outside of a preset calibration range.

24. The method of claim 19, wherein making the test measurement at a selected time comprises programming the wavefront sensing device to automatically make the test measurement on a set time frequency or event.

* * * * *